United States Patent [19]
Varsanyi et al.

[11] 3,966,961
[45] June 29, 1976

[54] METHANESULFONIC ACID-2-BROMOETHYL ESTER NEMATOCIDE

[75] Inventors: Denis Varsanyi, Arlesheim; Paul Rathgeb, Basel; Karl Gass, Magden, all of Switzerland

[73] Assignee: Ciba-Geigy Corporation, Ardsley, N.Y.

[22] Filed: Dec. 13, 1974

[21] Appl. No.: 532,432

[30] Foreign Application Priority Data
Dec. 21, 1973  Switzerland............... 18055/73

[52] U.S. Cl. ............................................. 424/303
[51] Int. Cl.² .......................................... A01N 9/14
[58] Field of Search .................................. 424/303

[56] References Cited
UNITED STATES PATENTS

| | | |
|---|---|---|
| 3,395,232 | 7/1968 | White ............................. 424/303 |
| 3,772,344 | 11/1973 | Tarnow et al. .................. 424/303 |
| 3,840,579 | 10/1974 | Fan ................................. 424/303 |

OTHER PUBLICATIONS
Chemical Abstracts, vol. 76 (1972), p. 126386t.

*Primary Examiner*—V. D. Turner
*Attorney, Agent, or Firm*—Harry Falber; Frederick H. Rabin

[57] ABSTRACT

Methanesulphonic acid-2-bromoethyl ester has been found to possess nematocidal properties. It may be used in the form of suitable compositions.

1 Claim, No Drawings

METHANESULFONIC ACID-2-BROMOETHYL ESTER NEMATOCIDE

The present invention relates to compositions and processes for the control of phytopathogenic nematodes by the use of a methanesulphonic acid ester as active substance.

Compounds that have hitherto assumed importance as nematocides are such compounds which act by way of the gas phase, such as, e.g., 1,2-dibromo-3-chloropropane and mixtures of dichloropropane and dichloropropene; or such compounds which undergo in the soil a rapid decomposition, such as, e.g., the sodium salt of monomethyldithio-carbamic acid or 3,5-dimethyl-tetrahydro-1,3,5-thiadiazine-2-thione.

The salt of monomethyl-dithiocarbamic acid is however storage-stable only as a solution of a specific concentration, and only as such has it the necessary stability; consequently, the much desired application thereof as a granulate or as a scattering agent has to be excluded. The smell nuisance created by application of the mentioned nematocides (dithiocarbamates), and the irritant effect of halogenated alkanes and alkenes enormously restrict the range of application of such compounds. The thiadiazine derivative at a practical level of concentration is inadequately effective.

Sulphonic acid esters have in numerous cases been suggested as pesticidal active substances for application in the protection of plants. There have recently been described haloalkyl esters of methanesulphonic acid as an antidote of herbicidal active substances for the protection of cereal plants (see DOS No. 2,141,586 and DOS No. 2,163,192).

It has now been found that the methanesulphonic acid-2-bromoethyl ester of the formula $$CH_3SO_2OCH_2CH_2Br$$

possesses excellent nematocidal properties, and has no disadvantages, such as irritant effect, high toxicity towards warm-blooded animals, instability in storage, an unpleasant smell, etc..

Methanesulphonic acid-2-bromoethyl ester is suitable for the control of phytopathogenic nematodes, such as those belonging, for example, to the following species: Meloidogyne spp., Heterodera spp., Ditylenchus spp., Pratylenchus spp., Paratylenchus spp., Anguina spp., Heliocotylenchus spp., Tylenchorhynchus spp., Rotylenchulus spp., Tylenchulus semipenetrans, Radopholus similis, Belonolaimus spp., Trichodorus spp., Longidorus spp., Aphelenchoides spp., Xiphinema spp. and Rhadinaphelenchus spp..

The nematocide according to the invention is not phytotoxic, and at the usually applied level of concentration, which is between 0.5 kg of active substance and 10 kg of active substance per hectare for the treatment of large areas, it does not impair in any way the growth of useful plants. The active substance can thus be used, for example, in the following cultivated crops: tobacco, potatoes, tomatoes, vegetables, grape-vines, maize, rice, soya beans, sugar beet, cotton, sugar cane, citrus fruits, bananas, pineapples, sweet potatoes, coffee, tea, cocoa and groundnuts. It can be used also in tree nurseries and for other ornamental plants. The applied concentration for such crops is preferably 1 to 8 kg of active substance per hectare (treatment of large areas).

The following tests serve to illustrate the nematocidal action of methanesulphonic acid-2-bromoethyl ester.

Nematocidal Test

To test the action against soil nematodes, the active substance is added in the concentration given in each case ($x$ ppm = $x$ parts of active substance in 1,000,000 parts of diluent) to soil and sand infested by root gall nematodes (Meloidogyne arenaria), and the whole is intimately mixed. In test series A, tomato seedlings are planted immediately in the soils prepared in this manner, and in test series B, tomato seeds are sown after a waiting period of one week.

For an assessment of the nematocidal action, the galls present on the roots are counted 28 days after planting and sowing, respectively.

Evaluation:
0 = complete nematocidal action = no infestation,
1 = slight infestation (a few small galls),
2 = fairly severe infestation (numerous galls, in some cases large ones),
3 = no nematocidal action = severe infestation as in the case of the control specimens (large galls).

| Active substance | Substrate | Test series A Concentration | | Test series B Concentration | |
|---|---|---|---|---|---|
| | | 25 ppm | 5 ppm | 25 ppm | 5 ppm |
| methanesulphonic acid-2-bromoethyl ester (active substance according to the invention) | soil | 0 | 0 | 0 | 0 |
| | sand | 0 | 0 | 0 | 0 |
| Comparative products: | | | | | |
| a) known from DOS 2,141,586 and DOS 2,163,192 | | | | | |
| ethanesulphonic acid-2-bromoethyl ester | soil | 0 | 2 | 0 | 2 |
| methanesulphonic acid-3-bromo-n-propyl ester | soil | 3 | 3 | 3 | 3 |
| | sand | 3 | 3 | 3 | 3 |
| methanesulphonic acid-2-chloroethyl ester | soil | 3 | 3 | 3 | 3 |
| | sand | 3 | 3 | 3 | 3 |
| chloromethanesulphonic acid-2-bromoethyl ester | soil | 3 | 3 | 3 | 3 |
| | sand | 3 | 3 | 3 | 3 |
| b) known from Beilstein, Vol. XI/II, page 20 | | | | | |
| benzenesulphonic acid-2-bromoethyl ester | soil | 3 | 3 | 3 | 3 |
| | sand | 3 | 3 | 3 | 3 |
| c) known from FR-PS 1,534,046 | | 100 ppm | | | |
| β-bromoethanesulphonic acid methyl | soil | 1* | — | — | — |
| d) known from US-PS 3,275,506 | | | | | |
| methanesulphonic acid-2-chloroethyl-thio ester | soil | 3 | — | — | — |
| e) Commercial products: | | | | | |
| O,O-diethyl-O-2,4-dichlorophenyl-thiophosphoric acid ester | soil | 3 | 3 | 3 | 3 |
| | sand | 3 | 3 | 3 | 3 |

-continued

| Active substance | Substrate | Test series A Concentration | | Test series B Concentration | |
|---|---|---|---|---|---|
| | | 25 ppm | 5 ppm | 25 ppm | 5 ppm |
| (known from US-Patent 2,761,806, under the trade name of "VC-13-Nemacide", Virginia-Carolina Chem. Corp.) 3,5-dimethyl-2-thio-tetrahydro-2H-1,3,5-thiadiazine (known under the trade name of "Dazomet") | soil sand | 3 3 | 3 3 | 3 3 | 3 3 |

*severe phytotoxicity

It is to be seen from the preceding list of products that the nematocidal action of methanesulphonic acid-2-bromoethyl ester, which action is excellent down to a low concentration, causes this ester to stand out from the series of nearest-related sulphonic acid esters. Even ethanesulphonic acid-2-bromoethyl ester is fully effective only at a concentration of 25 ppm. Also various carboxylic acid amides suggested in DOS No. 2,218,097 as herbicidal antidotes are shown to be ineffective or only slightly effective against soil nematodes.

Methanesulphonic acid-2-bromoethyl ester is known (see CAN. J. Chem. 34, 757-68 (1956). The compound has moreover at different times been investigated as a cytostatic drug and anticancer agent (see J. Chem. Soc. 1957, 2420–22; C.A. 61, 600 d (1964); C.A. 58, 6785 b (1963); C.A. 63, 8915 a (1963).

In these publications as well as in the German Offenlegungsschriften mentioned in the foregoing, there is to be found no reference to the possibility of using methanesulphonic acid-2-bromoethyl ester as a nematocide. One skilled in the art is in a certain sense discouraged by the published literature from using the compound as a nematocide. It was not therefore in any way to be anticipated, and was hence surprising that methanesulphonic acid-2-bromoethyl ester offers excellent possibilities of application as a nematocide.

For the control of soil nematodes, the active substance of the invention is used in the form of solid or liquid preparations. For application to the soil and for working into the soil, the preparations which are particularly advantageous are those that ensure a uniform distribution of the active substance through a layer of soil extending to a depth of 15 to 25 cm. The manner of application and the form of application are governed, in particular, by the type of nematodes to be controlled, by the climate and by the conditions of the soil. Since the new active substance is not phytotoxic at low concentrations, and does not impair germination power, it can be used, without any so-called period of restriction having to be observed, immediately before or after sowing of the plants. It is likewise possible to treat already existing cultivated crops with the new compositions. Furthermore, specific parts of plants, such as seed, sections of stalks (sugar cane) or bulbs, as well as roots or young plants, can be dressed with dispersions or solutions of the active substance in order to effect propagation.

Compositions according to the invention are produced, in a manner known per se, by the intimate mixing and grinding of the active substance with suitable carrier substances, optionally with the addition of dispersing agents or solvents which are inert to the active substance. The active substance can be obtained and used in the following forms:

solid preparations: dusts, scattering agents, granulates, coated granulates, impregnated granulates and homogeneous granulates;

water-dispersible concentrates of active substance: wettable powders and emulsions; solutions.

The particle size of the carrier substances is advantageously up to about 0.1 mm for dusts, about 0.075 to 0.2 mm for scattering agents, and 0.2 mm and over for granulates.

The concentration of active substance in the solid preparations is between 0.5 and 80%.

Solutions should contain the active substance at a concentration of between 1 and 20%.

Other biocidal active substances or compositions can be added to the described compositions of the invention. For the widening of their sphere of action, the new compositions can contain, in addition to the compound mentioned, for example, insecticides, fungicides, bactericides, fungistatics, bacteriostatics or other nematocides. The compositions according to the invention may also contain plant fertilisers, trace elements, etc.. Suitable known nematocides are, for example, the following: 0,0-diethyl-0-p-nitrophenyl-thiophosphate (PARATHION), 0,0-diethyl-0-[p-(methylsulphinyl)-phenyl]-thiophosphate (FENSULFOTHION, DASANIT), 0,0-diethyl-S-(ethylthio-methyl)-thiophosphate (PHORATE), 0,0-diethyl-0-(2-pyrazinyl)-thiophosphate (THIONAZIN, ZINOPHOS), 0,0-diethyl-0-(2-isopropyl-6-methyl-4-pyrimidinyl)-thio-phosphate (DIAZINON), 0-ethyl-S,S-di-n-propyl-dithiophosphate (MOCAP), 0-ethyl-0-[(4-methylthio)-m-tolyl]-isopropylphosphoric acid amide (METAPHENAMIPHOS, NEMACUR P), 0-ethyl-S-phenyl-ethylthio-phosphate (DYFONATE), 0-ethyl-S-)N-methoxy-N-methyl-carbamoylmethyl)-N-isopropylthiophosphoric acid amide (FCS-13), 0-(4-chlorophenyl)-N,N'-dimethyl-phosphoric acid diamide (HL-245), 0-methyl-S-methyl-phosphoric acid amide (MONITOR), 0-phenyl-N,N'-dimethyl-phosphoric acid amide (NELLITE), 0,0-diethyl-0-(2,4-dichlorophenyl)-thiophosphate (VC13), 0,0-diethyl-0-(3,5,6-trichloro-2-pyridyl)-thiophosphate (DURSBAN), S-methyl-1-(dimethylcarbamoyl)-N-[(methyl-carbamoyl)oxy]-thioformamide (DP 1410). 2-methyl-2-methylthio-propionaldehyde-0-(methylcarbamoyl)-oxime (ALDICARB), 2,3-dihydro-2,2-dimethyl-7-benzofuranyl-methylcarbamates (FURADAN, CARBOFURAN), 2,4-dimethyl-1,3-dithiolan-2-yl-formaldoxime-N'-methylcarbamate (TIRPATE), 3,5-dimethyl-4-dimethylamine-methyl-phenyl-N-methylcarbamate (WE 417), S-methyl-N-[(methylcarbamoyl)-oxy]-thioacetimide (METHOMYL, LANNATE), 4-chloropyridine-N-oxide (DU NEMA), tetrachlorothiophene PENTHENE), methanesulphonic acid-2,4-dipropylphenyl ester (SD 10,268), 1,2-dibromo-3-chloropropane (DBCP, NEMAGON).

Some combinations are distinguished by an extremely good nematocidal action.

These nematocides can be mixed with the nematocide according to the invention in every possible mixing proportion within the range of 1 : 100 to 100 : 1, together with carrier substances and/or dispersing agents. The form of application and the applied concentration, with regard to the total content of active substance, are dependent on the nematodes to be controlled in the crops being treated, and on the conditions of the soil. Among the given forms of preparation, which can contain the active substance either alone or together with other nematocides, the solid forms particularly preferred are dusts, scattering agents and granulates, and the liquid forms particularly preferred are solutions or emulsion concentrates.

The nematocide according to the invention can be sold commercially in the most varied types of packaging. It can be sold, for example, in containers on which are printed instructions:
 a. for the application of methanesulphonic acid-2-bromoethyl ester as nematocide;
 b. for the working up of the product to obtain the various preparations described in the following (dispersions, emulsions, solutions);
 c. for the concentrations to be applied, as has been mentioned in the foregoing; and/or
 d. for use on the crops mentioned.

Forms of preparation are described in the following. The term 'parts' denotes parts by weight.

Granulate:

The following substances are used to prepare a 5% granulate:
 5 parts of methanesulphonic acid-2-bromoethyl ester,
 0.5 parts of silicic acid,
 94.5 parts of ground limestone (particle size 0.4 to 0.8 mm).

The active substance is dissolved in a solvent, and this solution is sprayed on to ground limestone. The acetone is subsequently evaporated off in vacuo. The resulting granulate is used for the protection of plants; for example, it is used for the treatment of seed beds, vegetable crops, sugar beet crops, cotton crops, etc..

Dusts:

The following substances are used to obtain a 10% dust:
 10 parts of methanesulphonic acid-2-bromoethyl ester,
 5 parts of highly dispersed silicic acid,
 85 parts of talcum.

The active substance is mixed and ground with the carriers. The dusts obtained are used, for example, for the treatment of seed beds and crops of ornamental plants.

Emulsion concentrate:

The following ingredients are mixed together to obtain a 25% emulsion concentrate:
 25 parts of methanesulphonic acid-2-bromoethyl ester,
 5 parts of a mixture of nonylphenolpolyoxyethylene and calcium dodecylbenzenesulphonate ("Emullat P 140 HFP"),
 35 parts of isophorone-(3,5,5-trimethyl-2-cyclohex-en-1-one,
 35 parts of dimethylformamide.

This concentrate can be diluted with water to obtain emulsions of a suitable concentration. Such emulsions are suitable for the treatment of vegetable crops, cotton crops, sugar beet crops, etc..

Wettable powders:

The following ingredients are used to prepare a 40% wettable powder:
 40 parts of methanesulphonic acid-2-bromoethyl ester,
 1 part of dibutylnaphthalenesulphonic acid,
 5 parts of the sodium salt of ligninsulphonic acid,
 2 parts of a 1:1 mixture of Champagne chalk and hydroxyethylcellulose,
 27 parts of kaolin,
 25 parts of sodium aluminium silicate.

The active substance is intimately mixed, in suitable mixers, with the additives, and the mixture is ground on the appropriate mills and rollers. There are obtained wettable powders which can be diluted with water to give suspensions of any desired concentration. Such suspensions can be used, for example, on cotton, sugar beet, tobacco, citrus fruit, banana and vegetable crops.

What we claim:

1. A method of combatting pests of the class Nematoda which comprises applying to said pest a nematocidally effective amount of 2-bromoethylmethane sulphonate.

* * * * *